US006992216B2

(12) United States Patent
Bechtel et al.

(10) Patent No.: US 6,992,216 B2
(45) Date of Patent: Jan. 31, 2006

(54) CRYSTALLIZATION OF AMINO ACIDS USING ULTRASONIC AGITATION

(75) Inventors: Siegfried Bechtel, Lampertheim (DE); Matthias Rauls, Limburgerhof (DE); Richard Van Gelder, Speyer (DE); Seth C. Simpson, East Stroudsburg, PA (US)

(73) Assignee: Abbott GmbH & Co. KG, Wiesbaden (DE)

( * ) Notice: Subject to any disclaimer, the term of this patent is extended or adjusted under 35 U.S.C. 154(b) by 83 days.

(21) Appl. No.: 10/337,692

(22) Filed: Jan. 7, 2003

(65) Prior Publication Data

US 2003/0166726 A1    Sep. 4, 2003

Related U.S. Application Data

(60) Provisional application No. 60/346,684, filed on Jan. 7, 2002.

(51) Int. Cl.
*C07C 229/00* (2006.01)
(52) U.S. Cl. .................................... 562/447
(58) Field of Classification Search ............ 23/295 R; 562/445, 447, 554
See application file for complete search history.

(56) References Cited

U.S. PATENT DOCUMENTS 5,955,105 A * 9/1999 Mitra et al. ............. 424/464

FOREIGN PATENT DOCUMENTS

FR       1.389.840    *  1/1965

OTHER PUBLICATIONS

Gavezzotti, Angelo, "Are Crystal Structures Predictable?" Accounts of Chemical Research, vol. 27, pp. 309-314 (1994).*
Ratsimba et al, "Sonocrystallization: The End of Empiricism?" KONA, No. 17, pp. 38-48 (1997).*
Cier et al, "Action des Ultrasons sur les Acides Amines en Solution Aqueuse" Bulletin de la Societe de Chimie Biologique, vol. XLIII, No. 11, pp. 1229-1236 (1961).*
Hua and Hoffmann, "Optimization of Ultrasonic Irradiation as an Advanced Oxidation Technology" Environmental Science and Technology, vol. 31(8), pp. 2237-2243 (1997).*
Inez Hua, "Final Report and Accomplishments to Date: An Investigation of Homogeneous and Heterogeneous Sonochemistry for Destruction of Hazardous Waste" U.S. Department of Energy publication, HUA—Final Report 1996-2000, 45 pages, (2000).*
Loiacono and Osborne, "Crystal Growth From Solution Using Cynlindrical Seeds" Journal of Crystal Growth, vol. 43, pp. 401 405 (1978).*
Cier et al, "Action des Ultrasons sur les Acides Amines en Solution Aqueuse" Bulletin de la Societe de Chimie Biologique, vol. XLIII, No. 11, pp. 1229-1236 (1961) - English Translation -.*
Ashley, M.J., "Ultrasonics in Chemical Processing" (1974) *The Chemical Engineer*, Jun.:368-371.

(Continued)

*Primary Examiner*—James O. Wilson
*Assistant Examiner*—Zachary C. Tucker
(74) *Attorney, Agent, or Firm*—John D. Conway; Gayle B. O'Brien

(57) ABSTRACT

A method for reducing the particle size of amino acid crystals using ultrasound is discussed.

33 Claims, 3 Drawing Sheets

OTHER PUBLICATIONS

Belikov, A.M. et al., "Grain Size After Dynamic Recrystallization of Aluminium Subjected to Ultrasonic Loading" (1982) *Phy. Met. Metall.*, 54(3): 160-163.

Combes, E. et al., "Precipitation-stripping of Yttrium Oxalate Powders From Yttrium-loaded HDEHP Organic Solutions Using an Ultrasonic Stirrer" (1997) *Hydrometallurgy*, 46(1):1-12.

Gatumel, C. et al., "Nucleation Control in Precipitation Processes by Ultrasound"(1998) *KONA*, 16:160-169.

Martinez, K.C.L. et al., "Intensification of Paraffin Crystallization with Ultrasound" (1999) *Industrial Crystallization*, 14:1-11.

Mydlarz, K. et al., "The Narrowing of Crystal Size Distributions in a Sonicator-MSMPR Crystallizer System" (1991) *Chem. Eng. Comm.*, 104:291-305.

Saleh, S.I. et al., "Application of Ultrasonics as a Means of Particle Size Control" (1992) *International Conference on Pharmaceutical Technology*, 2:149-158.

Thibert, R. et al., "Morphic Features Variation of Solid Particles After Size Reduction: Sonification Compared to Jet Mill Grinding" (1988) *Intl. J. of Pharmaceutics*, 47:171-177.

"Ultrasonic Crystallizer" (1974) *Chemistry and Industry*Jun.: VII.

* cited by examiner

CRYSTALLIZATION OF AMINO ACIDS USING ULTRASONIC AGITATION

This application claims priority to U.S. provisional application No. 60/346,684, filed 7 Jan. 2002.

BACKGROUND OF THE INVENTION

There is scattered evidence in the literature for the use of ultrasound in crystallization methodologies. By and large, ultrasound is used in crystallization methods to avoid metastable supersaturations (e.g., with highly viscous melts), to increase the formation of isometric crystals (e.g., adipic acid), and to micronize particle sizes (e.g., in precipitation processes). Such effects from the application of ultrasound in crystallization processes are thought to result from the occurrence of cavitation bubbles that, on collapse, give rise to microscopic water jets that may destroy agglomerates or enforce turbulent mixing in otherwise static diffusion layers around crystals. Until now there is no consistent meaningful model that accounts for all effects observed.

Although the chemical effects of ultrasound have been known for a long time, intensive modern study in this area only began at the beginning of the 1980s. Ultrasound can intensify the heat transfer, the nucleation rate (N. Enomoto et al., *J. Mater. Sci.* 27, 5239 (1992)) and the growth rate of crystals. Nucleation can be induced in a crystal-free solution below the supersaturation point at which primary nucleation would normally occur. Ultrasound can also generate substantial quantities of secondary nuclei. One mechanism involves cavitation, which tends to be focused at discontinuities in the liquid medium, and so takes place on or near the crystal surfaces. The intense forces of the collapse of cavitation bubbles can result in significant secondary nucleation. The mechanism by which ultrasound affects crystal growth is less well understood, but there may be a significant effect of acoustic streaming, providing enhanced mass transfer close to the crystal surface. More recently, it has been suggested that high-intensity sound initiates nucleation and helps to control crystal size and habit to yield products that better meet users' specifications (L. J. McCausland, *Chem. Eng. Progress*, pp. 56–61 (July 2001)).

In the pharmaceutical industry, there is a need for a low cost, efficient and effective large-scale method for reducing the particle size of pharmaceutically active ingredients. The particle size of a pharmaceutical ingredient may advantageously affect the properties of the ingredient, for example, by permitting preparation of dosage forms with improved dissolution or content uniformity.

SUMMARY OF THE INVENTION

In one embodiment, the invention pertains to a process for crystallizing an amino acid. The process includes subjecting a solution of an amino acid, such as L-thyroxine, to ultrasonic agitation at a temperature and for a period of time sufficient to produce a crystalline form of the amino acid having a reduced particle size as compared to a particle size of a crystalline form of the amino acid obtained without ultrasonic agitation.

In another embodiment, the invention also pertains, at least in part, to a process for crystallizing sodium L-thyroxine. The process includes subjecting an aqueous solution of sodium L-thyroxine to ultrasonic agitation while the solution is cooled to a temperature and for a period of time sufficient to produce a crystalline form of the sodium L-thyroxine having a particle size less than about 18 microns.

In a further embodiment, the invention pertains, at least in part, to a crystalline salt of L-thyroxine having a particle size less than about 18 microns. The crystalline salt is prepared by a process, which includes subjecting an aqueous solution of an L-thyroxine salt to ultrasonic agitation while the solution is cooled to a temperature and for a period of time sufficient to produce a crystalline form of the L-thyroxine salt having a particle size less than about 18 microns.

DETAILED DESCRIPTION OF THE INVENTION

I. Definitions

Figure 1:
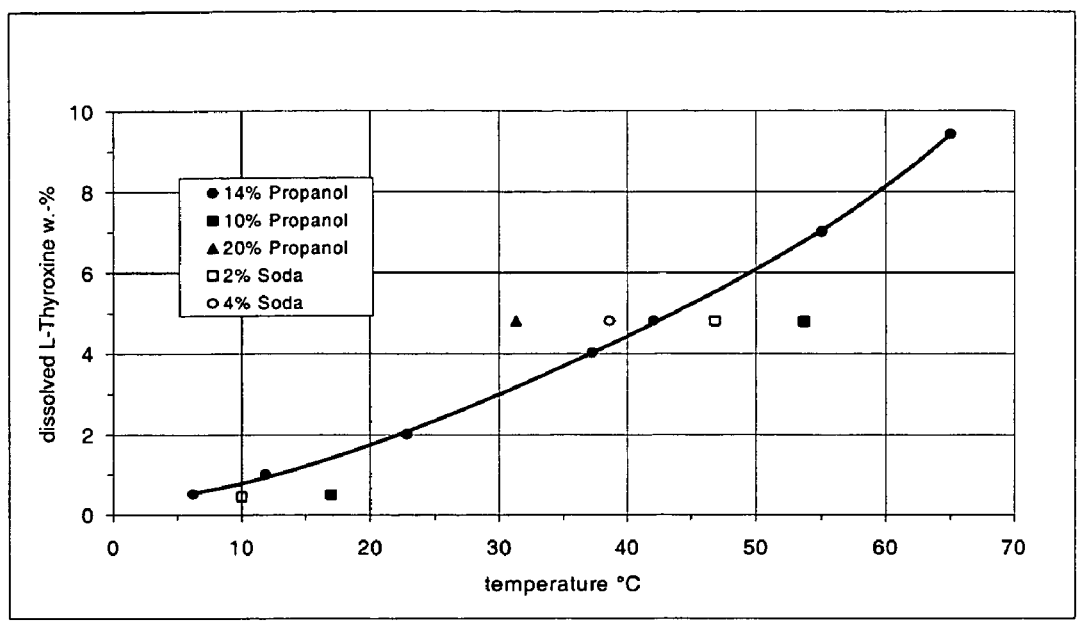
FIG. 1 is a line graph showing the solubility of sodium L-thyroxine in an aqueous solution containing 14.0% (w/w) propanol.

Before further description of the invention, certain terms employed in the specification, examples and appended claims are, for convenience, collected here.

The term "amino acid" includes compounds with both an amino group (e.g., $NH_2$ or $NH_3+$) and a carboxylic acid group (e.g., COOH or COO—). In an embodiment, the amino acid is not part of a polypeptide. The amino acid may be an α-amino acid, a β-amino acid, a D-amino acid or an L-amino acid. The amino acid may be a naturally occurring amino acid (e.g., alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, or histidine) or it may be a derivative thereof. Examples of derivatives include amino acids with one or more substitutions.

The term "crystalline form" includes solid forms of the amino acid that have a crystal lattice structure of molecules.

The term "dosage form" includes forms of the amino acid that are suitable for therapeutic administration to animals, preferably humans.

The term "high intensity ultrasonification" includes ultrasonification at a power greater than about 1.0 watt/$cm^2$ of power.

The term "low intensity ultrasonification" includes ultrasonification at a power not greater than about 1.0 watt/$cm^2$ of power.

The term "metastable zone" includes the range of temperatures to which a solution of an amino acid can be cooled without crystals forming. The upper range of the metastable zone can be determined experimentally by heating a cooled solution slowly to a temperature that is sufficient to dissolve the last remaining crystal. The lower range of the metastable zone can be determined by cooling a solution without crystals and recording the temperature at which the first crystals appear.

The term "nucleation temperature" includes the temperature at which crystals are formed in the solution. In one embodiment, the nucleation temperature of the solution of the amino acid exposed to ultrasonic agitation is raised as compared to the nucleation temperature of a solution of the amino acid which is not exposed to ultrasonic agitation. In one embodiment, the nucleation temperature of the solution is about 32 to about 42° C.

The term "pharmaceutically acceptable salts" is art recognized and includes relatively non-toxic, inorganic and organic acid addition salts of the amino acids of the present invention. These salts can be prepared in situ during the final isolation and purification of the amino acids of the invention, or by separately reacting a purified amino acid of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19). Preferably, the pharmaceutically acceptable salt of the invention is the sodium salt.

The term "reduced particle size" includes particle sizes that are smaller than the particle sizes obtained through the same process without ultrasonic agitation. In a further embodiment, the reduced particle size is determined by a volume measurement. The particle size is determined by the average particle size of a particular population of amino acid crystals.

The term "tyrosine derivative" includes α-amino acids and salts thereof which comprise the amino acid tyrosine with one or more substitutions, e.g., a substitution of a hydrogen for another atom. Examples of tyrosine derivatives include compounds with halogen substitutions, e.g., iodine substitutions, and aryl substitutions, e.g., at the hydroxy group of the tyrosine. In an advantageous embodiment, the tyrosine derivative is an aryl derivative of tyrosine, e.g., L-thyroxine, levothyroxine, or a pharmaceutically acceptable salt thereof.

The term "ultrasonic agitation" includes agitation by sound vibrations at a frequency beyond the limit of audible frequencies. The term "ultrasonic agitation" includes both low and high intensity ultrasonic agitation. One example of an apparatus for carrying out ultrasonic agitation is described in U.S. Pat. No. 5,471,001, incorporated herein by reference. Another example of an apparatus for carrying out ultrasonic agitation is described in (L. J. McCausland, *Chem. Eng. Progress*, pp. 56–61 (July 2001). Other examples for carrying out ultrasonic agitation on a laboratory scale include, but are not limited to, introducing an ultrasonic probe to a solution or immersing the solution in an ultrasonic bath (Martinez et al., *Industrial Crystallization* (1999) 1.

II. Processes of the Invention

In one embodiment, the invention pertains to a process for crystallizing an amino acid. The process includes subjecting a solution of the amino acid to ultrasonic agitation at a temperature and for a period of time sufficient to produce a crystalline form of the amino acid having a reduced particle size as compared to a particle size of a crystalline form of the amino acid obtained without agitation.

In an advantageous embodiment, the amino acid is subjected to ultrasonic agitation at a temperature and for a period of time sufficient to produce reduced-size particles of the amino acid that have properties that are more advantageous than particles of the amino acid obtained without ultrasonic agitation. Such advantageous properties permit the production of dosage forms of the amino acid with improved dissolution, content uniformity or both. Other advantages include, but are not limited to, higher bioavailability, manipulation of crystal size distribution, better process control through controlled nucleation, and a higher reproducibility of product quality.

The solution of the amino acid advantageously may contain from about 2 to about 6% of the amino acid, e.g., L-thyroxine. In certain embodiments, the solution may contain small seed crystals of the amino acid to facilitate the crystallization process. In a further embodiment, the solution may comprises about 11 to about 17% of an alcohol, such as, but not limited to, lower alkyl alcohols. Examples include n-propanol, n-butanol, i-propanol, ethanol, etc. The solution may also contain an amount of a salt, such as, for example, sodium carbonate, potassium carbonate, etc. The salt may comprise about 2 to 4% of the total weight of the solution. Preferably, the solution is aqueous.

In an advantageous embodiment, the amino acid is an α-amino acid or a derivative thereof, e.g., a tyrosine derivative. In a further embodiment, the amino acid is an aryl tyrosine derivative. Preferably, the amino acid is L-thyroxine or a pharmaceutically acceptable salt thereof. One example of an advantageous pharmaceutically acceptable salt is the sodium salt of L-thyroxine. L-thyroxine is a compound of the formula:

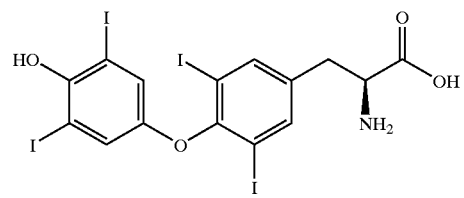

In a further embodiment, the tyrosine derivative is a hydrate of a salt of L-thyroxine, e.g., the sodium salt of L-thyroxine pentahydrate. L-thyroxine can be synthesized by methods shown in the art such as, for example, those described in U.S. Pat. No. 5,917,087.

The ultrasound agitation may be applied either in pulses or for a single application, during the crystallization process. Preferably, the ultrasound is applied at a frequency, intensity, power, or for a duration such that the particle size of the crystallized amino acid is reduced. In one embodiment, the ultrasonic agitation is carried out at a frequency sufficient to form crystals of the desired particle size. For example, the intensity of agitation may be selected such that it is sufficient to begin the onset of transient cavitation (i.e., "threshold intensity"), and has a sufficient power density, such that a reduced particle size of a crystalline form of an amino acid is formed. In one embodiment, the frequency of the agitation is about 10 to about 100 kHz; in another embodiment, about 20 to about 30 kHz.

The power density can be enhanced by increasing the intensity value of the agitation (e.g., $W/cm^2$), or by maintaining the threshold intensity across an increased surface area. In one embodiment, the intensity of the agitation is sufficient such that crystals of the desired particle size are formed. In a further embodiment, the intensity of the ultrasonic agitation is about 0.01 $W/cm^2$ to about 1.5 $W/cm^2$.

The power of the ultrasonic agitation may be applied at a sufficient power such that the crystals of the desired size are formed. For example, the ultrasonic agitation may be applied at a power of about 5 to about 2500 watts or higher (e.g., for larger volumes of solution of the amino acid).

Advantageously, the power of the ultrasonic agitator is selected appropriately for a desired volume. For instance, a small volume may require less power than a larger, plant scale vessel. For example, a 50-watt generator was used for a 22-liter lab vessel and a 2,000-watt generator was used for a 1200-gallon plant vessel. In an embodiment, the ultrasonic agitation produced by a transducer. In a further embodiment, the ultrasonic agitation may be applied (continuously or in pulses) for a period sufficient to reduce the particle size of the crystalline form of the amino acid formed. In a further embodiment, the ultrasonic agitation may be applied for a period of about two hours or more.

In accordance with the invention, the solution of the amino acid may be cooled while it is subjected to ultrasonic agitation. Thus, in one embodiment, the ultrasonic agitation is applied as the solution is cooled from above the nucleation temperature of said amino acid to below the nucleation temperature of the amino acid. The nucleation temperature for amino acids of the invention may range from about 32 to about 42° C. In a further embodiment, the ultrasonic agitation is applied while the solution is cooled from about 40 to about 50° C. down to about 30 to about 35° C. In another embodiment, the ultrasonic agitation is applied while the solution is cooled from about 40 to about 50° C. down to about 10 to about 20° C.

In another embodiment, the solution is cooled at a rate such that the size of the particle size of the crystalline form of the amino acid is reduced. In an embodiment, the solution is cooled at a rate of greater than about 0.1° C. per minute, or, preferably, at a rate of greater than about 0.4° C. per minute. In a further embodiment, the solution is cooled from about 40 to about 50° C. down to below the nucleation temperature.

In another embodiment, the solution of the amino acid is subjected to ultrasonic agitation for a period of time sufficient to reduce a metastable zone of the solution, such that the particle size of the crystalline form is reduced as compared with crystalline form of the amino acid not subjected to the ultrasonic agitation. In a further embodiment, the metastable region is reduced by about 1° C. to about 5° C.

In another embodiment, the mean reduced particle size of the crystalline form of the amino acid is less than about 18 microns, less the about 12 microns, less than about 10 microns, or less than about 7 microns. In one advantageous embodiment, the mean reduced particle size of the crystalline form of the amino acid is between about 5 and about 18 microns, between about 6 and about 12 microns, or, advantageously, between about 6.1 and about 8 microns.

The process also may comprise other techniques, which do not adversely affect the formation of a crystalline form of the amino acid having a reduced size being formed. For example, in a further embodiment, the process may comprise stirring the solution, e.g., with a motorized stirrer or stir bar. In a further embodiment, the solution is stirred with a stirrer having an energy sufficient to enhance the formation of crystals; for example, the stirrer may have an energy greater than a 5 watt/kg.

In a further embodiment, the invention pertains, at least in part, to a process for crystallizing sodium L-thyroxine. The method includes subjecting an aqueous solution of sodium L-thyroxine to ultrasonic agitation. The solution is then cooled to a temperature and for a period of time sufficient to produce a crystalline form of the sodium L-thyroxine having a particle size less than about 18 microns.

In yet another embodiment, the invention pertains to a crystalline salt of L-thyroxine having a particle size less than about 18 microns. The crystalline salt is prepared by a process comprising subjecting an aqueous solution of an L-thyroxine salt to ultrasonic agitation while the solution is cooled to a temperature and for a period of time sufficient to produce a crystalline form of the L-thyroxine salt having a particle size less than about 18 microns.

EXEMPLIFICATION OF THE INVENTION

The invention is further illustrated by the following examples that should not be construed as limiting.

EXAMPLE 1

Solubility of L-Thyroxine

The solubility of L-thyroxine was determined by studying a standard solution of L-thyroxine. The standard solution consisted of the materials listed in Table 1:

TABLE 1

| L-Thyroxine: | 50.0 kg | 4.84% | w of anhydrous LT4/w |
|---|---|---|---|
| water | 809.7 kg | 78.4% | w/w |
| n-propanol | 144.2 kg | 14.0% | w/w |
| sodium carbonate | 29.5 kg | 2.85% | w of monohydrate/w |

The L-thyroxine solution was then transferred to a glass crystallizer and cooled until the L-thyroxine crystallized spontaneously. Then, the temperature of the solution was slowly raised until the crystallized L-thyroxine was redissolved. The crystallization status of the solution was determined using a light probe. The light probe was comprised of two parallel rods with a light source and a photocell. The light probe measured the amount of crystals in the solution by determining the change in the amount of light that was absorbed or scattered by the solution. In solutions with crystals, the photocells registered a weakened beam as compared to beams sent through clear solutions.

Data obtained from these experiments is plotted in FIG. 1. The solubility of L-thyroxine in the standard solution is given by black circles, interpolated by the solid line.

The temperature of saturation at standard conditions (4.84% w/w) was 42° C. (108° F.) and the solubility at the end of the cooling curve (10° C., 50 F) was 0.78%. A theoretical yield of 83% of L-thyroxine was calculated. Other experiments have shown that a reduction of sodium carbonate or propanol content of the initial solution reduces L-thyroxine solubility (light gray symbols) and, thus, enabled higher yields. However at higher sodium carbonate or propanol concentrations (dark gray symbols), the inverse effect is observed. At a concentration of 20% propanol or 4% sodium carbonate, the solubility of L-thyroxine at lower temperatures was not determined. Under these conditions, sodium carbonate co-precipitated with sodium L-thyroxine at around 10° C.

It was found that L-thyroxine solubility and yield were dependent on solution composition. Concentrations of L-thyroxine above 10% were not feasible due to degradation at above 65° C. It was found that lower propanol and sodium carbonate content gave higher yields of L-thyroxine, while higher concentrations of propanol or sodium carbonate lead to sodium carbonate precipitation.

EXAMPLE 2

Parametric Sensitivity of L-Thyroxine Crystallization

The following trials were conducted to test the effects of various parameters other than ultrasonification on the crystallization of L-thyroxine. These trials were performed in a one liter glass crystallizer equipped with three baffles and a 60 mm marine type propeller (Ne=0.4). While most trials were run with the standard solution given in Example 1, propanol concentration was varied in trials 5 and 6. The final temperature for all trials was 10° C. The parameters of the 10 trials are summarized in Table 2.

TABLE 2

| # | Cooling rate k/h | Power Input [W/kg] | Drying Pressure [mbar] | Drying temp ° C. | Solid Content % | Water Content % | Particle size μm | Remarks |
|---|---|---|---|---|---|---|---|---|
| 1 | 20/10 | 0.5 | 1013 | 25 | 3.1 | 10.1 | 30 | Crystals dried openly in lab |
|   |       |     | 10   | 50 |     | 3.1  | 15 |  |
| 2 | 20/10 | 5   | 10   | 35 | 3.3 | —    | 18 | stirrer rate increased 3× |
| 3 | 30    | 0.5 | 10   | 35 | 3.4 | 5.5  | 19 |  |
| 4 | 30    | 5   | 1013 | RT | 3.4 |      | 10 |  |
| 5 | 30    | 5   | 50   | 35 | 2.2 |      | <20 μm | 20% propanol |
| 6 | 30    | 5   | 50   | 35 | 5.2 |      | >30 μm | 10% propanol |
| 7 | 30    | 0.5 | 1013 | RT | 3.3 |      | 16 | 2*1:1 rinsed with 90/10 EtOH/water |
| 8 | 30    | 5   | 50   | 35 | 3.4 |      | 11 | 2*1:1 rinsed with 90/10 EtOH/water |
| 9 | 30    | 2   | 50   | 35 | 3.6 |      | 13 | 2*1:1 rinsed with 90/10 EtOH/water |
| 10| 30    | 0.5 | 50   | 35 | 3.7 |      | 15 |  |
|   |       |     | 50   | 35 | 3.7 |      | 15 | 1 hour stirring |
|   |       |     | 50   | 35 | 3.7 |      | 15 | 2 hour stirring |

Figure 2:
FIG. 2 is a digital image showing crystals of sodium L-thyroxine obtained by cooling the sodium L-thyroxine solution under ambient conditions.

In trial 1, the effect of cooling rate was studied. It was found that when the crystals were dried at room temperature and pressure, the resulting crystals were large (30 μm) and had a water content of 10.1%. A digital image of these crystals is shown in FIG. 2. When the crystals were dried at elevated temperature (50° C.) and decreased pressure (10 mbar), the resulting crystals were about half the size (15 μm) and were dried far below the water content for the stable pentahydrate (3.1% water versus 10.1% for the pentahydrate).

In trial 2, the stirrer rate was increased threefold from the standard conditions. The resulting crystals were 18 μm as compared to 30 μm under the standard conditions.

In trial 3, the cooling rate was increased to 30 K/h. This resulted in a reduction of particle size to 19 μm. However, the crystals were overdried and only had about 50% of the theoretical water content.

Figure 3:
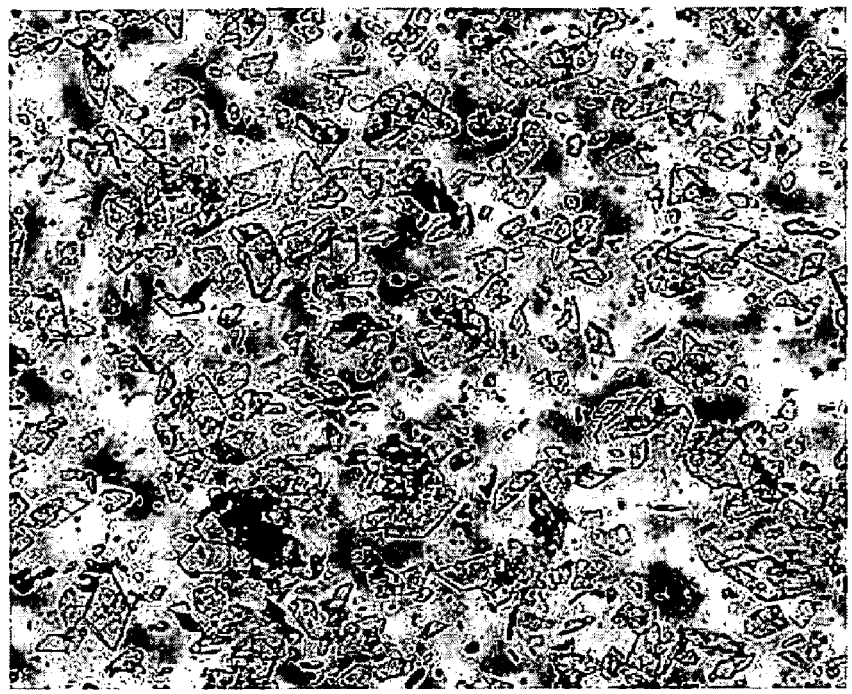
FIG. 3 is a digital image showing crystals of sodium L-thyroxine obtained with a 30 K/h cooling rate and a stirrer energy of 5 W/kg.

In trial 4, the 30 K/h cooling rate was combined with the 5 W/kg stirrer energy. This combination reduced the particle size to 10 μm. A digital image of the crystals obtained in trial 4 is shown in FIG. 3.

Figure 4:
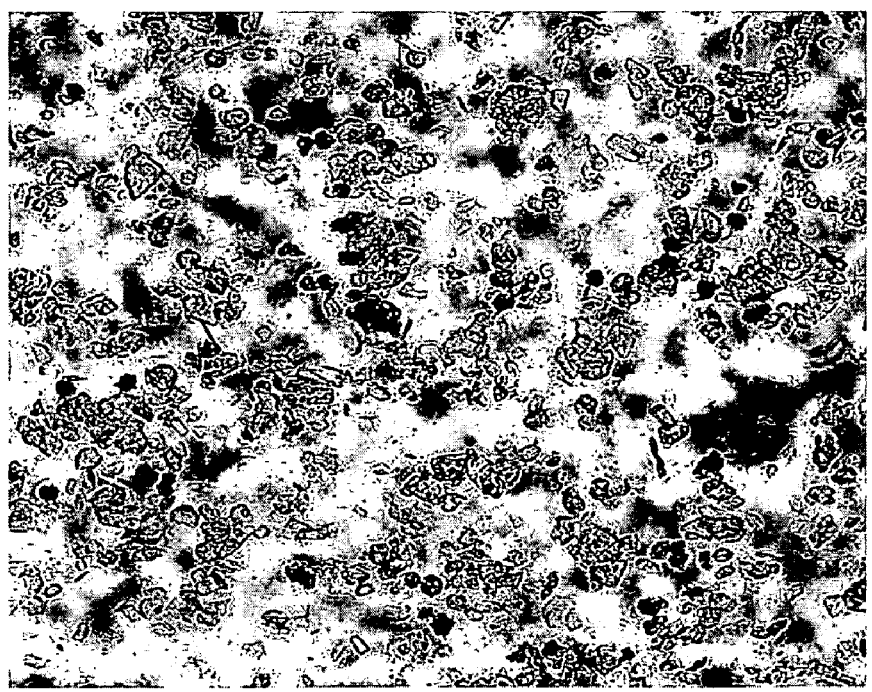
FIG. 4 is a digital image showing crystals of sodium L-thyroxine obtained by increasing the propanol concentration of the standard solution to 20%.

In trial 5, the effect of increasing the propanol concentration to 20%, with other conditions as described for trial 4, was studied. This trial produced very fine crystals (<<20 μm, see FIG. 4), but the yield was less than 50%.

Figure 5:
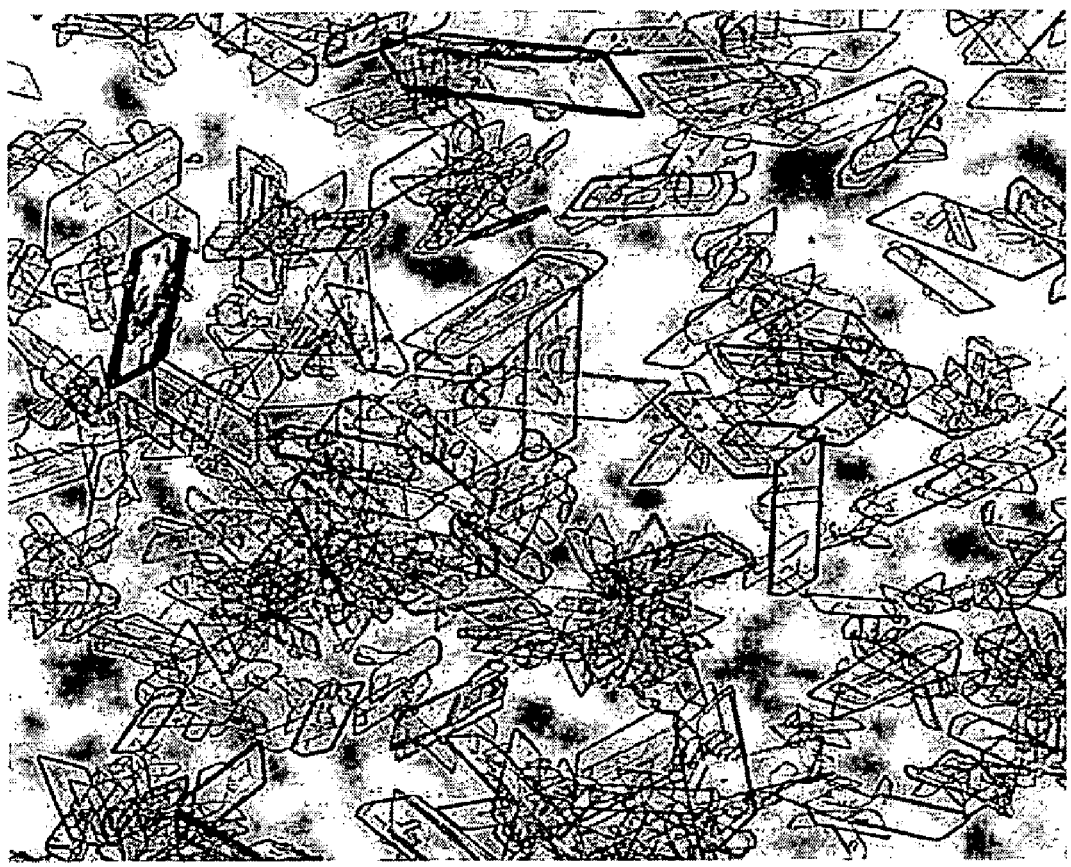
FIG. 5 is a digital image showing crystals of sodium L-thyroxine obtained by decreasing the propanol concentration of the standard solution to 10%.

Trial 6 tested the effect of the propanol concentration to 10% (w/w), with other conditions as described for trial 4. The crystal yield of trial 6 reached 100% of the expected yield. The resulting crystals are shown in FIG. 5. Despite the harsh crystallization conditions, the resulting crystals were large and elongated.

Trials 7, 8, and 9 tested the effect of increasing stirrer power. The trials were run with stirrer powers of 0.5, 2 and 5 W/kg respectively. It was found that sizes of the crystals decreased (16, 13, 11 μm) with increasing stirrer power.

In trial 10, the stirring time of the solution at the final temperature was increased. The length of stirring time did not affect crystal size nor change the yield.

In summary, the trials showed that L-thyroxine crystals are sensitive to abrasion and breakage by stirrer contact. Crystals of 10 μm were produced at stirrer power inputs of 5 W/kg and cooling rates of 30 K/h. Low propanol content of the crystallization solution produces large, elongated crystals even under harsh crystallization conditions. It was also found that the L-thyroxine crystals became overdried at 35° C., but retained their natural water content at 25° C. When the crystals were severely overdried (50° C./3,3% water), finer particles were produced by breakage.

EXAMPLE 3

Effect of Ultrasonification on the Crystallization of L-Thyroxine

In this example, the effect of ultrasonification on the crystallization of L-thyroxine was analyzed.

L-thyroxine crystals were obtained by batch-wise cooling crystallization of a standard solution of L-thyroxine. The standard solution consisted of the materials listed in Table 3:

TABLE 3

| L-Thyroxine: | 50.0 kg | 4.84% | w of anhydrous LT4/w |
| water | 809.7 kg | 78.4% | w/w |
| n-propanol | 144.2 kg | 14.0% | w/w |
| sodium carbonate | 29.5 kg | 2.85% | w of monohydrate/w |

To crystallize L-thyroxine, the standard solution of L-thyroxine was heated to a specified temperature, introduced into a crystallizer and cooled at a controlled rate. As the solution cooled and L-thyroxine crystallized, the solution was exposed to ultrasonification.

A sonotrode complete with generator and transducer capable of emitting an radial ultrasonic pressure wave at a 20 kHz frequency and 2000W of power (UIP 2000 industrial processor with block sonotrode) was mounted in the crystallizer. The L-thyroxine solution was prepared and agitated at 20 RPM. The temperature was stabilized at 50° C., and the ultrasonic generator was turned on in continuous mode and at 100% amplitude. The cooling sequence was then initiated and the temperature of the solution was lowered at 0.5° C. per minute to a final set point of 10° C. The period of time that the ultrasound was applied to the solution as it was cooling to this set point was varied. For the first trial, a controlled crystallization was allowed to occur without any application of ultrasound to the product solution. For the second trial, the ultrasound remained on until a temperature of 30° C. was reached. At this point the ultrasound was turned off while the solution continued to cool to 10° C. When 10° C. was reached, the slurry was sampled and heated back up to 50° C. to redissolve the solid. The third trial proceeded in the same manner, but when the solution reached a temperature of 26° C., the ultrasound was turned off and the solution continued to cool to 10° C. The trials continued in this manner, changing the temperature at which the ultrasound was turned off by 4° C. each time until for the last trial, the solution was sonified throughout cooling. During this last trial, ultrasound was maintained at the cooling set point for a period of one hour, with samples being pulled at the half hour and one hour mark. This slurry was then transferred to a filter dryer for filtering, washing and drying. Once the product was dry, a sample was taken to determine the additional effects on particle size of the manufacturing process downstream of the crystallizer.

The example was repeated to determine reproducibility. For this example, two crystallization trials were performed; a crystallization without ultrasound and a crystallization with ultrasound applied continuously throughout the cooling period. Both of these trials had heating and cooling temperature set points of 50° C. and 10° C., respectively. The slurry produced with ultrasound was also transferred to another vessel for filtering, washing and drying at 35° C. Once the product was dry, it was sampled and then allowed to come to ambient temperature while it was continually agitated at 6 RPM for a period of one hour. After this one-hour period, a sample was again obtained from the filter dryer. This was done in an effort to determine the effects of prolonged agitation during drying on the particle size of L-thyroxine.

Particle size analysis for all samples was performed with an Aerosizer aerodynamic time-of-flight particle-sizing instrument.

The experimental conditions and results of the crystallization trials performed during the first batch are given in Table 4 below.

Samples for all of the trials shown in the table above were taken from the crystallizer in the slurry form. A portion of these slurry samples was filtered, washed with ethanol and dried at ambient temperature. A reduction in particle size on a volume basis was apparent between trial 1, which underwent no sonification, and trials 2–7, which underwent various periods of ultrasound application. The magnitude of this reduction is roughly three fold.

The effect on particle size of the length of time that the solution was exposed to ultrasound after the point of nucleation was a point of interest during these experimental trials. The point of nucleation of the aqueous solution of sodium L-thyroxine observed was approximately 32° C. in the absence of ultrasound. In the second trial, ultrasound was switched off at 30° C. Thus, ultrasound was applied past the expected point of nucleation for the duration of time that it took the solution to cool 2° C. This trend was followed, varying the temperature by 4 degrees, in multiple recrystallizations until ultrasound was left on during the entire cooling cycle. No observable change in particle size on a volume or number basis occurred.

EXAMPLE 4

Effect of Changes in Width of Metastable Zone on L-Thyroxine Crystallization

L-thyroxine aqueous solutions have been shown to exhibit metastable zones (a range of supercooling) of approximately 5–11° C. during cooling. The extent of the metastable zone depends on the rate of cooling. The lower the cooling rate, the higher the temperature at which nucleation begins. The table below shows the temperature at which solid formation was visible during cooling of the solutions in the trials.

TABLE 5

| Trial # | Ultrasound | Nucleation Temperature (° C.) |
| --- | --- | --- |
| 1 | off | 25 |
| 2 | on | 35 |
| 3 | on | 38 |
| 4 | on | 38 |
| 5 | on | 34 |
| 6 | on | 36 |
| 7 | on | 34 |

This example indicated a decrease in the metastable zone for the sonified solution of approximately 1–3° C. at a cooling rate of 0.17–0.5° C. per minute. During the plant scale experimentation, with a cooling rate of 0.5° C. per minute, an increase of 9–18° C. was observed in the temperature at which solids appeared during the sonified crys-

TABLE 4

| Trial #1 | Ultrasound | Temperature Ultrasound turned on (° C.) | Temperature Ultrasound turned off (° C.) | Mean Particle Size Volume | Mean Particle Size (Number) |
| --- | --- | --- | --- | --- | --- |
| 1 | off | N/A | N/A | 20.8 | 3.0 |
| 2 | on | 50 | 30 | 6.6 | 2.4 |
| 3 | on | 50 | 26 | 5.4 | 2.3 |
| 4 | on | 50 | 22 | 5.7 | 2.5 |
| 5 | on | 50 | 18 | 5.3 | 2.4 |
| 6 | on | 50 | 14 | 5.2 | 2.4 |
| 7 | on | 50 | 10 | 6.1 | 3.1 | tallizations. Although the recording of these temperatures was subjective, a distinct narrowing of the metastable zone was observed when ultrasound was introduced.

EXAMPLE 5

Effect of Intensity of Ultrasonification on Crystal Size

A one-liter round bottom glass flask was filled with the standard L-thyroxine solution and cooled under stirring. The flask was then immersed in an ultrasonic bath (Sonorex Super Bandelin DK102, ≈40 kHz) to study the influence of different sonification intensities on the size of L-thyroxine crystals. The frequency and power dissipated by the bath was measured using a hydrophone. As an additional parameter, the onset point of sonification and its duration was also varied. The relevant experimental parameters and results are summarized in Table 6:

TABLE 6

| # Trial | Ultrasonification Intensity | Undercooling [° C.] | Average Size [µm] | C.V. |
| --- | --- | --- | --- | --- |
| 1 | 0% US | 13.6 | 46 | 74 |
| 2 | 10% US | 12.1 | 13 | 70 |
| 3 | 10% US 32.5° C. | 12.8 | 11 | 84 |
| 4 | 50% US | 10.6 | 13 | 65 |
| 5 | 50% US 32.5° C. | 12.5 | 11 | 69 |
| 6 | 100% US | 11.9 | 11 | 61 |
| 7 | 100% US 32.5° C. | 12.5 | 11 | 62 |
| 8 | 100% US/off | 10.9 | 22 | 74 |

% US: relative intensity of the ultrasonic bath (100% corresponds to roughly 0.18 W/cm$^2$)
Undercooling: Difference between the point of nucleation and the saturation temperature
US 32.5° C.: US was switched on 1K above expected nucleation temperature
US/off: US was switched off immediately after nucleation occurred
C.V. Coefficient of variation = $(X_{86} - X_{14})/(2 * X_{50})$, it is a measure for the broadness of the particle size distribution)

It was observed that even low intensities of ultrasound reduced the size of L-thyroxine crystals from 46 to 13 µm. No significant additional reduction in particle size was achieved by increasing the intensity of ultrasound beyond an intensity of 10%.

EXAMPLE 6

Effects of Intensity of Ultrasonification on Crystal Size

In order to verify the findings from Example 5, additional experiments were carried out in a 22 L double jacket glass crystallizer equipped with a draft tube and a 200 mm marine type propeller (Ne=0.3). A custom-made sonotrode (24 kHz) was used along with a UIP250 sound generator. In this example, the exact sonification power was not determined, although it was estimated to be in the order of 25–50 W. The findings are illustrated in Table 7.

TABLE 7

| Trial # | Ultrasound | Crystal size |
| --- | --- | --- |
| 1 | No Ultrasound | 28 µm |
| 2 | 10% Ultrasound | 15 µm |
| 3 | 100% Ultrasound | 14 µm |

As shown in Table 7, it was found that even smallest ultrasound intensity the particle size by 50%, with no additional effect at full power.

Incorporation by Reference

The entire contents of all patents, published patent applications and other references cited herein are hereby expressly incorporated herein by reference Equivalents Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A process of crystallizing L-thyroxine comprising subjecting a solution of L-thyroxine or a salt thereof to ultrasonic agitation at a temperature and for a period of time sufficient to produce a crystalline form of said L-thyroxine.

2. The process of claim 1, wherein said L-thyroxine is a sodium salt of L-thyroxine.

3. The process of claim 1, wherein said solution of said L-thyroxine is subjected to ultrasonic agitation while being cooled.

4. The process of claim 1, wherein said solution of said L-thyroxine is subjected to ultrasonic agitation for a period of time sufficient to reduce a metastable zone of said solution by about 1° C. to about 5° C.

5. The process of claim 1, wherein the mean particle size of said L-thyroxine is less than about 18 microns.

6. The process of claim 5, wherein said mean particle size of said L-thyroxine is less than about 12 microns.

7. The process of claim 6, wherein said mean particle size of said L-thyroxine is less than about 10 microns.

8. The process of claim 7, wherein said mean particle size of said L-thyroxine is less than about 7 microns.

9. The process of claim 1, wherein the mean particle size of said L-thyroxine is between about 5 and about 18 microns.

10. The process of claim 9, wherein said mean particle size of said L-thyroxine is between about 6 and about 12 microns.

11. The process of claim 10, wherein said mean particle size of said L-thyroxine is between about 6.1 and about 8 microns.

12. The process of claim 1, wherein said solution comprises crystals of L-thyroxine.

13. The process of claim 12, wherein said solution comprises about 2 to about 6% L-thyroxine.

14. The process of claim 1, wherein said solution comprises about 11 to about 17% n-propanol.

15. The process of claim 1, wherein said solution comprises about 2 to about 4% sodium carbonate.

16. The process of claim 1, wherein said solution comprises an aqueous mother liquor.

17. The process of claim 1, wherein said ultrasonic agitation is applied in periodic pulses.

18. The process of claim 1, wherein said ultrasonic agitation is applied continuously.

19. The process of claim 1, wherein said ultrasonic agitation is at a frequency of about 20 to about 50 kHz.

20. The process of claim 1, wherein said ultrasonic agitation is at an intensity ranging from about 0.01 W/cm$^2$ to about 0.3 W/cm$^2$.

21. The process of claim 1, wherein the source of said ultrasonic agitation is a transducer.

22. The process of claim 1, wherein the ultrasonic agitation is applied at a power of between about 5 and about 50 watts.

23. The process of claim 2, wherein said ultrasonic agitation is applied while said solution is cooled from above the nucleation temperature of said amino acid to below the nucleation temperature of said amino acid.

24. The process of claim 23, wherein said nucleation temperature ranges from about 32 to about 42° C.

25. The process of claim 2, wherein said solution is cooled a rate of greater than about 0.1° C. per minute.

26. The process of claim 1, wherein said ultrasonic agitation is applied for at least about 2 hours.

27. The process of claim 1, wherein said ultrasonic agitation is applied while said solution is cooled from about 40 to about 50° C. down to below the nucleation temperature.

28. The process of claim 2, wherein said ultrasonic agitation is applied while said solution is cooled from about 40 to about 50° C. down to about 30 to about 35° C.

29. The process of claim 2, wherein said ultrasonic agitation is applied while the solution is cooled from about 40 to about 50° C. down to about 10 to about 20° C.

30. The process of claim 1, further comprising stirring the solution.

31. The process of claim 1, wherein the solution is stirred with stirrer having an energy greater than a 5 watt/kg.

32. A process for crystallizing sodium L-thyroxine, comprising subjecting an aqueous solution of sodium L-thyroxine to ultrasonic agitation while the solution is cooled to a temperature and for a period of time sufficient to produce a crystalline form of the sodium L-thyroxine having a particle size less than about 18 microns.

33. The process of claim 1, wherein the process results in dosage forms of the amino acid with improved dissolution or content uniformity or both.

* * * * *

UNITED STATES PATENT AND TRADEMARK OFFICE
CERTIFICATE OF CORRECTION

PATENT NO. : 6,992,216 B2  Page 1 of 1
APPLICATION NO. : 10/337692
DATED : January 31, 2006
INVENTOR(S) : Siegfried Bechtel et al.

It is certified that error appears in the above-identified patent and that said Letters Patent is hereby corrected as shown below:

Column 14, lines 17-20, claim 33 should be deleted in its entirety.

Signed and Sealed this

Tenth Day of April, 2007

JON W. DUDAS
*Director of the United States Patent and Trademark Office*